United States Patent [19]

Johnson et al.

[11] Patent Number: 4,550,201

[45] Date of Patent: Oct. 29, 1985

[54] ORGANOPHOSPHORUS ENAMINES USEFUL AS EPOXY CURATIVES AND ADHESION PROMOTERS

[75] Inventors: Milton D. Johnson; Mohinder S. Chattha, both of Livonia, Mich.

[73] Assignee: Ford Motor Company, Dearborn, Mich.

[21] Appl. No.: 685,377

[22] Filed: Dec. 24, 1984

[51] Int. Cl.⁴ .................................. C07F 9/53
[52] U.S. Cl. ........................................ 564/15
[58] Field of Search ........................... 564/15

[56] References Cited

U.S. PATENT DOCUMENTS

| | | | |
|---|---|---|---|
| 3,442,948 | 5/1969 | Wiley | 564/15 |
| 3,518,262 | 6/1970 | Maier | 564/15 X |
| 4,196,149 | 4/1980 | Frank et al. | 564/15 |
| 4,225,512 | 9/1980 | Frank et al. | 564/15 |
| 4,278,811 | 7/1981 | Frank et al. | 564/15 |

OTHER PUBLICATIONS

M. S. Chattha and A. M. Aquir, "Organophosphorus Enamines IV., Enamine Thiophosphonates; Preparation and Their Attempted Use in the Synthesis of $\alpha,\beta$--Ethylenic Ketones", J/Org. Chem., 36, 2892, (1971).

J. Skolimowski, M. Simalty, "Organic Compounds of Phosphorus:XII[1], Ammonium Acetate/Acetic Acid, A Reagent for the Direct Heterocyclization of Bis-and Tris 1-Alkynyl Phosphine Oxides", Synthesis, No. 2, (1979).

M. S. Chattha, "Novel Organophosphorus Heterocyclic Compounds: 1-Ethoxyphosphoryl-3,5-Disubstituted-4-Aza-Cyclohexa-2,5-Dienes, Chemistry and Industry, No. 4, 157, (1980).

Primary Examiner—Earl Nielsen
Attorney, Agent, or Firm—Lorraine S. Melotik; Roger L. May

[57] ABSTRACT

This invention is directed to organophosphorus compounds useful as epoxy curing agents and adhesion promoters.

6 Claims, 2 Drawing Figures

Fracture Energy ($G_c$) vs. Time Of Immersion In Water, At 60°C.
A - DGEBA Cured With DETA;
B - Enamine 3 As Primer And DGEBA Cured With DETA;
C - DGEBA Cured With Enamine 2.

ORGANOPHOSPHORUS ENAMINES USEFUL AS EPOXY CURATIVES AND ADHESION PROMOTERS

TECHNICAL FIELD

This invention relates to a class of organophosphorus enamines, i.e., compounds which contain both amino and pentavalent phosphorus moieties. They may be prepared by the nucleophilic addition of amines to the activated triple bonds of tris(alkynyl-1)phosphine oxide or tris(alkynyl-1)phosphine sulfide. These organophosphorus enamines react with epoxy resins to form thermoset materials while providing improved adhesion of the resin material to polar substrates, e.g., glass.

BACKGROUND OF THE INVENTION

Adhesive and paint compositions have been applied to polar substrates, such as glass, cellulose and ceramic materials. However, the bond between the composition and the polar substrate is often subject to failure under conditions of stress, high humidity, and elevated temperatures. Adhesion promoters are often incorporated into such compositions or coated on the substrate to improve the adhesion of the composition to the substrate. Typical of such adhesion promoters for polymeric compositions are silanes.

As is known in the art, incorporating a polar functional group, such as pentavalent phosphorus, into a polymer increases the adhesion of the polymer to polar substrates. Amines and other species having lone pairs of electrons are also known to coordinate strongly to polar surfaces. Additionally, amines are known as epoxy curing agents. We have now synthesized a class of epoxy curing agents containing both amino and pentavalent phosphorus moieties and found them useful as adhesion promoters for epoxy resins. Thus, these organophosphorus enamines may be employed to cure epoxy resins while providing improved adhesion of the resin to the substrate. On the other hand, materials such as silanes, while promoting adhesion of an epoxy composition to the substrate, may not be used as the sole curing agent for epoxy materials since they react only to a limited extent with the epoxy resin.

DISCLOSURE OF THE INVENTION

This invention is directed to organophosphorus enamine compounds useful as epoxy curing agents and adhesion promoters. These enamines comprise compounds having the general chemical formula:

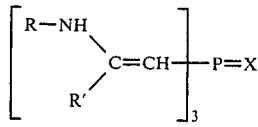

wherein X is oxygen or sulfur, R' is an alkyl or aryl group and R is the same or different alkyl group. R may be substituted with non-interferring functionality, such as an amine group.

This invention is also directed to a method for making these organophosphorus enamines which comprises reacting tris(alkynl-1)phosphine oxide with aliphatic amines. Still further, this invention is directed to compositions comprising epoxy resins and these organophosphorus enamines.

As mentioned above, it has now been found that these enamine compounds may be employed to cure epoxy compositions while providing improved adhesion of the composition to polar substrates, such as glass. This improved adhesion of the composition to the substrate provides improved resistance to failure of the composition-substrate bond under conditions of stress, high humidity and elevated temperatures. Additionally, it has been found that incorporation of even small amounts of these compounds into epoxy compositions cured with conventional amines provides improved adhesion of the composition of the substrate. Still further, application of the organophosphorus enamines as primers on the polar substrate to be coated with, e.g., conventially amine cured epoxy compositions also provides improved resistance to adhesive failure of the composition-substrate bond under these conditions.

DETAILED DESCRIPTION OF THE INVENTION

Figure 1:
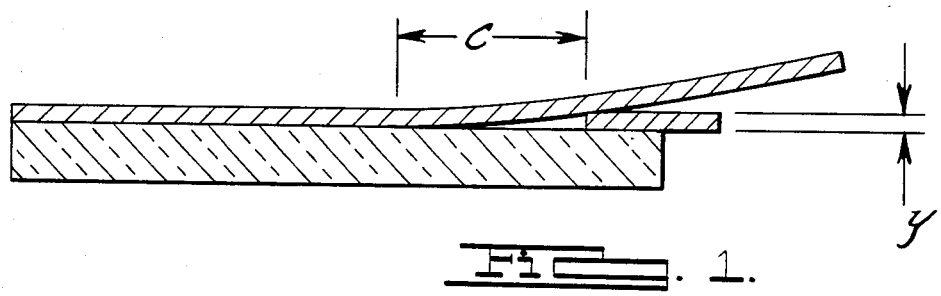
FIG. 1 illustrates the fracture energy test configuration.

This invention is directed to organophosphorus enamines comprising compounds having the general chemical formula:

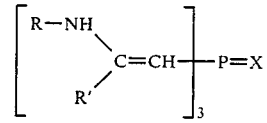

wherein X is oxygen or sulfur, R' is an alkyl or aryl group and R is the same or different alkyl group. Still further R may be substituted with any non-interferring functionality, e.g., a tertiary, secondary or primary amine, aryl, hydroxyl, ester and ether group. The particular R' and R of the organophosphorus enamines are determined by the organic groups present in the materials used to form the enamine. Preferably, R and R' are organic groups having about 1 to about 9 carbon atoms.

The organophosphorus enamine may be formed by means of the following two step reaction sequence. The first step of the sequence comprises preparing a tris(alkynl-1)phosphine compound. This phosphine compound may be formed by reacting anhydrous 1-alkyne with an organolithium compound, generally in solution, to form an alkynyllithium reaction product which is subsequently reacted with phosphorus oxychloride or phosphorus thiochloride. Use of the phosphorus oxychloride results in a phosphine oxide compound being formed while the use of the phosphorus thiochloride results in the formation of a phosphine sulfide compound. The alkyne is reacted with an organolithium compound in about a 1.3–1:1 molar ratio, preferably in about a 1.1–1:1 molar ratio. Any unreacted 1-alkyne may be removed by distillation under reduced pressure. It is necessary to react all of the organolithium compound since unreacted organolithium will react with the phosphorus compounds. The alkynyllithium and the phosphorus compound are reacted in at least about a 3:1 molar ratio.

The second step of the reaction sequence for forming the enamine comprises reacting the phosphine compound produced according to the first step with amines containing at least one primary aliphatic amines group. These amines include monofunctional amines and polyfunctional amines. The phosphine compound, i.e., oxide or sulfide, and the amine are reacted in amounts which provide at least 3 moles of amines relative to each mole of the phosphine compound. Preferably, a molar excess of the amines, i.e., greater than the 3:1 molar ratio, are provided with the phosphine compound in this second reaction step. Any excess amine which may be present after completion of reaction with the phosphine compound may be distilled off under reduced pressure. The organophosphorus enamine product produced is generally a viscous, oily material.

The enamines of this invention may also be made by the process described above except that Girgnard Reagent materials, such as organomagnesium bromide, are used instead of the organolithium compound. Exemplary of such materials are alkyl magnesium bromides, such as methyl magnesium bromide, propylmagnesium bromide and butyl magnesium bromide. Use of the organolithium compound for making the enamines is preferred.

The anhydrous 1-alkyne employed in the process for making the organophosphorus enamines as described above may include materials such as 1-propyne, 1-butyne, 1-pentyne, 1-hexyne, 1-nonyne, and phenylacetylene, preferably those 1-alkynes containing between about 3 and 11 carbon atoms. As would be apparent to one skilled in the art, mixtures of various 1-alkynes may also be used.

The organolithium compound reacted with the 1-alkyne includes, but is not limited to, alkyl lithium compounds such as methyllithium, ethyllithium, butyllithium, pentyllithium, and hexyllithium, with butyllithium being most preferred.

Phosphorus oxychloride and phosphorus thiochloride are materials well known in the art.

The primary aliphatic amines employed in making the organophosphorus enamine may be any aliphatic amine containing at least one primary aliphatic amine group, i.e., primary amine attached to an aliphatic group. It may be substituted with other functionalities such as secondary or tertiary amine, hydroxyl, ester, ether and thioether groups. These amines include, but are not limited to, monoamines such as n-butylamine, hexylamine, cyclohexylamine, and benzylamine and polyfunctional amines such as diethylenetriamine, hexamethylenediamine, isophoronediamine, and triethylenetetramine. In those instances where amines having more than one primary aliphatic amine are employed, some oligomer formation may occur since each primary amine can react with the phosphine compound. However, a majority of the product comprises enamines formed from reaction of only one of the primary amines of the amine with the phosphine compound. Such reaction, i.e., of only one of the primary amine groups of the amine can be further assured by employing amine in excess of the 3:1 molar ratio of the amine:phosphine compound, as taught above.

In one embodiment of the process described above, anhydrous 1-pentyne, is reacted with n-butyllithium. The reaction product thereof is subsequently reacted with phosphorus oxychloride to form the first reaction step material, i.e., tris(pentynyl-1)phosphine oxide. The chemical reactions of this first step are depicted in the following chemical equations:

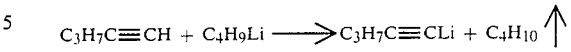

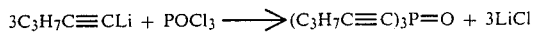

This first reaction step material is then reacted with n-butylamine, until the IR spectrum shows a complete disappearance of the C≡C absorption. Disappearance of this absorption indicates that all of the alkynyl phosphine oxide has been reacted to form the enamine. This second reaction step is chemically described according to the following equation:

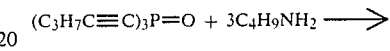

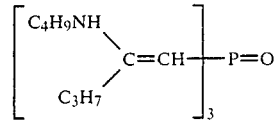

If a polyfunctional aliphatic amine, such as diethylene triamine had been used instead of the n-butylamine, the following equation would describe the second step reaction.

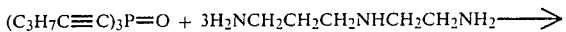

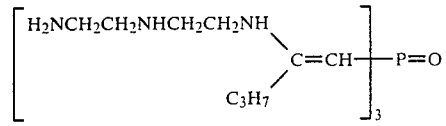

Organophosphorus enamines react with epoxy resins to produce hard cured materials. When monoamines are employed to make the enamines, the major curing reaction taking place is epoxy ring opening by the imino function. In the case of those enamines formed from polyfunctional amines, both amino and imino groups would participate in the epoxy curing reactions.

The invention will be further understood by referring to the following detailed examples. It should be understood that the specific examples are presented by way of illustration and not by way of limitation.

EXAMPLE 1

Synthesis of tris(pentynyl-1)phosphine oxide (1)

Anhydrous 1-pentyne (10.2 g, 0.15 mol) is dissolved in 750 ml anhydrous diethyl ether and placed under nitrogen in a two liter, three necked flask. The flask is cooled with dry ice and a 2.4M solution (62.5 ml, 0.15 mol) of n-butyllithium in hexane is added slowly with continuous stirring. The reaction mixture is stirred for one hour and a solution of phosphorus oxychloride (7.17 g, 0.05 mol) in 100 ml diethyl ether is added dropwise with continuous stirring and cooling. After the addition is complete, the reaction mixture is allowed to warm slowly (1 hour) to 0° C. It is stirred for an additional half hour and is worked up by slowly adding 150 ml cold water. The layers are separated and the aqueous layer is extracted with two 50 ml portions of chloroform. The combined organic extracts are dried over anhydrous magnesium sulphate and the solvent is stripped after filtration. The oily residue is shortpath distilled under reduced pressure to obtain 10.5 g (84%) of the desired product 1.

EXAMPLE 2

Synthesis of tris(2-diethylenetriamine-1-pentenyl)phosphine oxide: Enamine (2)

This material is prepared by treating one gram of the phosphine oxide (1) produced in Example 1 with four grams of diethylenetriamine (DETA). The initial reaction is exothermic; however, the addition goes to completion only after heating for one hour at 90° C. as evidenced by disappearance of the C≡C IR absorption (2190 cm$^{-1}$).

Tensile strength determination

The tensile strengths of glass to steel bonds formed from bisphenol-A diglycidyl ether (DGEBA) cured with Enamine (2) are compared to those of DGEBA cured with DETA alone. Stoichiometric amounts of the curing agents, based on active amino hydrogens, are employed. The test samples are prepared by bonding annealed glass panels (7.62 cm×2.54 cm×0.476 cm) to sanded steel strips (10.2 cm×0.64 cm×0.068 cm) by curing the adhesives at 120° C. for one half hour; the bond area is 0.64 cm×0.64 cm. Tensile lap shear strengths are determined by pulling the samples to bond failure at room temperature using an Instron Mechanical Tester. The samples are aged in 100% humidity at 60° C. The tensile strengths of samples before and after aging are listed below:

| Curing Agent | Exposure Time, hours | Shear Strength KPa |
| --- | --- | --- |
| DETA | 0 | 22,000 |
| DETA | 24 | 6,200 |
| DETA | 48 | 4,800 |
| Enamine 2 | 0 | 22,000 |
| Enamine 2 | 24 | 15,200 |
| Enamine 2 | 48 | 13,800 |

Stress corrosion test

Bonds formed from the two adhesive compositions employed for the tensile strength determination described above, i.e., DGEBA cured with Enamine 2 and DGEBA cured with DETA, are evaluated under stress in the presence of water. Test samples are prepared using glass slides (7.62 cm×2.54 cm×0.122 cm) and steel strips (10.2 cm×0.635 cm×0.068 cm) cut from a 30.5 cm×10.2 cm panel with Bonderite 37 treatment. One side and edge of the panel are marked before cutting with a shear; the strips are always oriented the same. In this way, the variability due to slight metal deformation when the strips are cut is minimized. The steel strips are bonded to the glass leaving approximately 0.6 cm nonbonded length at the end. The samples are cured by placing them in an oven at 90° C. for one half hour. The excess adhesive along the edges of the metal is removed using a razor blade.

The thickness of the metal and glass are measured. A clamp is positioned 1.5 cm from the edge of the glass to prevent the crack from traveling too far when the crack is initiated; the glass and metal are forced apart a distance sufficient to insert a spacer 7 mm thick as shown in FIG. 1. The spacer is removed and the distance from the bottom of the glass at the edge to the top of the metal is measured. The spacer is reinserted and the distance remeasured; the difference gives the effective thickness of the spacer. This method of measuring thickness, y, eliminates any variability due to bending which might occur. After removing the clamp, the location of the crack tip is observed by holding the specimen between the cross polaroids and observing the edge of the glass. The blue spot due to maximum stress concentration shows the end of the crack. The specimens are then immersed in water at 60° C. and the length of the crack, c, is measured after various intervals of time.

Figure 2:
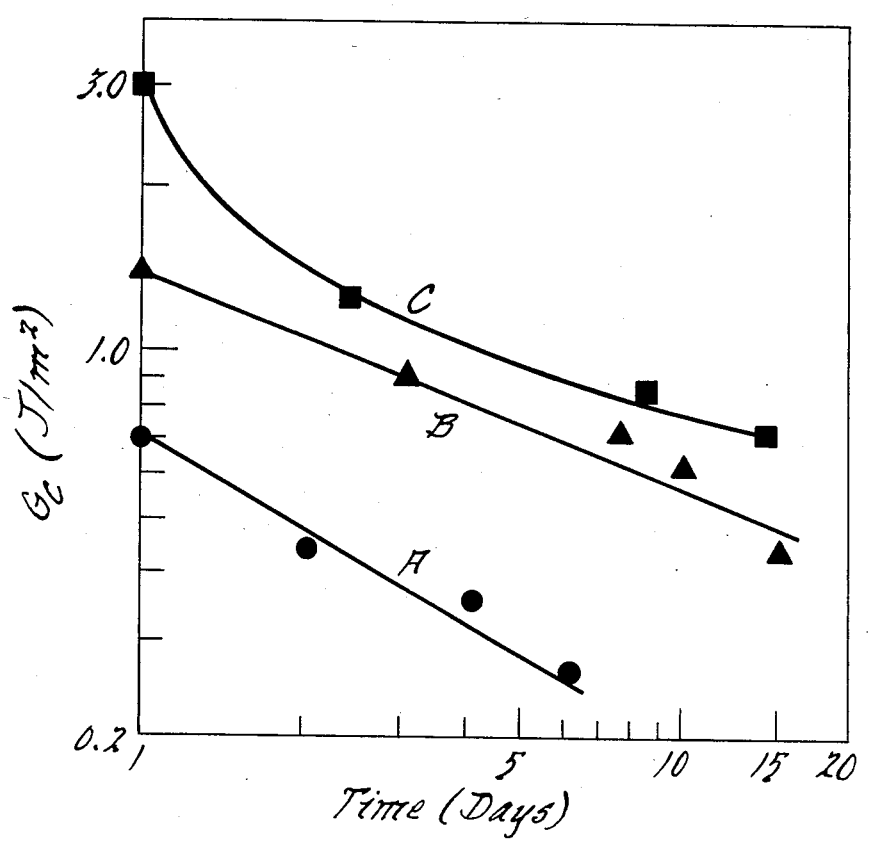
FIG. 2 graphically illustrates the fracture energy ($G_c$) vs time of immersion in water at 60° C. for various adhesive materials.

For a constant spacer height, y, the stresses at the root of the crack decrease as the crack grows. The amount of stress that the bond can withstand determines its resistance to cleavage. Hence, if after a certain length of time, t', the crack length is found to be c', the stresses existing at the root of the crack represent the resistance of the adhesive bond to failure in the time t'. Rather than computing the stresses at the root of the crack, an equivalent quantity, the fracture energy, is computed (Corten, H. T., "Fracture Mechanics of Composites", Chapter 9 in Liebowietz, H., ed. Fracture, Vol. VII, Academic Press, New York, b 1972). For the test specimen, this is given by:

$$\text{Fracture Energy } (G_c) = \frac{3E_1 h_1^3}{8} \left[ \frac{y^2}{c^4} \right] \left[ \frac{1}{1 + \frac{E_1 h_1^3}{E_2 h_2^3}} \right]$$

where
$E_1$ = modulus of steel
$h_1$ = thickness of the steel
$E_2$ = modulus of glass
$h_2$ = thickness of the glass
y = thickness of the wedge cap
c = length of the crack The changes in fracture energy with time of immersion in water at 60° C. are shown in FIG. 2 where line A is that for DGEBA cured with DETA and curve C gives results obtained using DGEBA cured with Enamine 2. DGEBA cured with Enamine 2 has a higher initial $G_c$ than that of DGEBA cured with DETA and continues to perform better throughout the testing.

EXAMPLE 3

Synthesis of tris(2-n-butylamino-1-pentenyl)phosphine oxide: Enamine (3)

In a reaction flask, 10 g. of phosphine oxide (1) produced in Example 1 is dissolved in 100 ml n-butylamine; even though an initial exothermic reaction occurs, the IR after one hour of mixing shows that addition of amine to the triple bonds is incomplete. The mixture is refluxed for one hour and the IR spectrum shows complete disappearance of the C≡C absorption (2190 cm$^{-1}$) and appearance of a very strong C=C absorption (1610 cm$^{-1}$). This indicates that the reaction of the amine with the phosphonic oxide of Example 1 is complete. The excess amine is distilled off under reduced pressure using a water aspirator and its last traces are removed by using a vacuum pump to obtain the desired product in quantitative yield as a viscous oily material.

Adhesion Testing of Enamine Used as Primer

Enamine (3) produced in this example, is used as a primer to coat a glass surface prior to bonding with DGEBA cured with DETA. This DGEBA-DETA composition was made like that of Example 2, wherein stoichiometric amounts of the curing agents, based on active amino hydrogen, are employed. Prior to bonding, the glass plate is dipped in a 1% solution of Enamine (3) in ethyl acetate. The plate is removed from the solution and the solvent is allowed to evaporate at room temperature for one hour. Glass to metal bonds are then prepared and tested as described in Example 2. Line B in FIG. 2 shows the results obtained with the glass coated with Enamine 3. Compared to line A, DBEBA cured with DETA and no treatment of the glass surface, line B shows improved adhesive performance with Enamine 3 as primer.

Determination of Epoxy Resin Cure With Enamine (3)

An adhesive composition is made from 1.2 g of DGEBA mixed with 1.29 g of Enamine (3) made in Example 3. This composition is placed in an oven at 125° C. for one hour to obtain a hard transparent material. Thermal gravimetric analysis of this material shows that it does not decompose up to 260° C.

EXAMPLE 4

Anhydrous 1-octyne (16.5, 0.15 mol) is dissolved in 750 ml anhydrous diethyl ether and the preparation of tris(octynyl-1)phosphine oxide is carried out as described in Example 1. The reaction mixture is worked up by adding 200 ml of sodium chloride aqueous solution. The layers are separated and the aqueous layer is extracted with two 50 ml portions of chloroform. The combined organic extracts are dried over anhydrous sodium sulfate and the solvent is distilled off after filtration. Last traces of the solvent are removed under vacuum. Octynyl phosphine oxide is obtained as a light yellow oily product.

The above product (1.1 g) is reacted with four grams of DETA as described in the synthesis of Example 2 to produce Enamine (4). The adhesive samples are prepared and the tensile strength is determined as described in Example 2. The tensil strengths of samples before and after aging in 100% relative humidity at 60° C. are listed below.

| Curing Agent | Exposure Time, Hrs. | Shear Strength KPa |
| --- | --- | --- |
| DETA | 0 | 23,500 |
| DETA | 24 | 6,700 |
| DETA | 48 | 5,200 |
| Enamine 4 | 0 | 23,500 |
| Enamine 4 | 24 | 16,800 |
| Enamine 4 | 48 | 14,100 |

EXAMPLE 5

Phenyl acetylene (15.3) is dissolved in 800 ml anhydrous ether and is reacted with equimolar amount of n-butyllithium as described in Example 1. A solution of thiophosphoryl chloride (8.4 g) in 100 ml diethyl ether is added dropwise to phenylethynyllithium with continuous stirring and cooling. After the addition is complete, the reaction mixture is allowed to warm to 0° C. It is stirred for an additional half hour and is worked up by slowly adding 200 ml of saturated sodium chloride solution. The layers are separated and the aqueous layer is extracted with two 75 ml portions of chloroform. The combined organic extracts are dried over anhydrous potassium carbonate and the solvent is evaporated after filtration. The oily residue produces light yellow crystals upon standing at room temperature.

One gram of phenylethynylphosphine sulfide was reacted with 4.2 g diethylenetriamine, according to the enamine synthesis procedure described in Example 2, to produce Enamine (5). Adhesive compositions and test samples are prepared as described in Example 2. The tensile strengths of the samples before and after aging in 100% relative humidity at 60° C. is determined and the same pattern of shear strength retention is seen as in Example 4.

EXAMPLE 6

Phenylethylnylphosphine sulfide (2 g) from Example 5 is refluxed in 50 ml n-butylamine according to the enamine synthesis procedure of Example 3. The enamine obtained is evaluated as an adhesion promoter for glass according to the testing described in Example 3. The test samples with Enamine (6) primer display superior adhesive performance to those without the primer.

While particular embodiments of the invention have been described, it will be obvious to those skilled in the art that various changes and modifications may be made without departing from the invention, and it is intended to cover in the appended claims all such modifications and equivalents as fall within the true spirit and scope of this invention.

What is claimed is:

1. Organophosphorus enamine compounds useful as epoxy curing agents and adhesion promoters, said organophosphorus enamine comprising compounds having the general chemical formula:

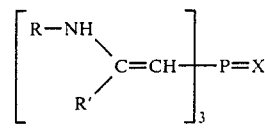

wherein X is oxygen or sulfur, R' is an alkyl or aryl group and R is the same or different alkyl group.

2. Compounds according to claim 1, wherein R bears amino functionality.

3. Compounds according to claim 1, wherein said R and R' are selected from organic groups having between about 1 to about 9 carbon atoms.

4. A process for preparing organophosphorus enamine compounds which comprises reacting:
 (A) tris(alkyne-1)phosphine compound made by reacting:
  (a) 1-alkyne;
  (b) organolithium compound; and
  (c) phosphorus compound selected from phosphorus oxychloride and phosphorus thiosulfide;
  wherein (a) and (b) are reacted in a molar ratio of about 1.3-1:1 to form an alkynllithium reaction product subsequently reacted with (c) in at least about a 3:1 molar ratio; and
 (B) primary aliphatic amine,
wherein said phosphine compound (A) and said primary aliphatic amine (B) are reacted in amounts which provide at least a 3:1 molar ratio of said amine relative said phosphine compound.

5. A process according to claim 4, wherein said 1-alkyne is selected from 1-alkyne compounds comprising 3 to 11 carbon atoms.

6. A process according to claim 4, wherein said primary aliphatic amines are selected from aliphatic monofunctional amines and aliphatic polyfunctional amines.

* * * * *